United States Patent [19]

Walter

[11] 4,081,544
[45] Mar. 28, 1978

[54] CERTAIN 2-(ALPHA(2-PYRIDYL)-BENZYL)IMIDAZO-LINES AND DERIVATIVES THEREOF

[75] Inventor: Lewis A. Walter, Madison, N.J.

[73] Assignee: Schering Corporation, Kenilworth, N.J.

[21] Appl. No.: 754,396

[22] Filed: Dec. 27, 1976

Related U.S. Application Data

[60] Continuation of Ser. No. 637,498, Dec. 4, 1975, abandoned, which is a division of Ser. No. 412,852, Nov. 5, 1973, Pat. No. 3,932,431, which is a continuation of Ser. No. 49,578, Jun. 24, 1970, Pat. No. 3,770,737, which is a continuation of Ser. No. 704,263, Feb. 9, 1968, abandoned.

[51] Int. Cl.² ............... A61K 31/45; A61K 31/425; A61K 31/495
[52] U.S. Cl. .................... 424/263; 424/250; 424/251; 424/270; 424/273 R; 424/275; A61K/31/505
[58] Field of Search ............... 424/250, 251, 263, 270, 424/273, 275

[56] References Cited

U.S. PATENT DOCUMENTS 2,656,358   10/1953   Sperber et al. ................. 260/296 R
3,770,737   11/1973   Walter ............................. 260/250 R

OTHER PUBLICATIONS

Chem. Abst., vol. 76, Abst No. 59632e, (1972).
Chem. Abst., vol. 55–col 3590 (1961).

*Primary Examiner*—Stanley J. Friedman
*Attorney, Agent, or Firm*—Raymond A. McDonald; Stephen B. Coan

[57] ABSTRACT

The present 2-substituted imidazolines and 2-substituted-3,4,5,6-tetrahydropyrimidines possess valuable antidepressant and anti-inflammatory properties. The compounds are prepared by the condensation of an appropriately substituted nitrile with a diamine. For example, condensation of 2-pyridylbenzyl cyanide with 1,2-ethylene diamine or with 1,3-propylene diamine produces a 2-(2-pyridylbenzyl) imidazoline or a 2-(2-pyridylbenzyl)-3,4,5,6-tetrahydropyrimidine.

16 Claims, No Drawings

CERTAIN 2-(ALPHA(2-PYRIDYL)-BENZYL)IMIDAZOLINES AND DERIVATIVES THEREOF

This application is a continuation application of Ser. No. 637,498, filed Dec. 4, 1975, now abandoned, which in turn is a divisional application of Ser. No. 412,852, filed Nov. 5, 1973, now U.S. Pat. No. 3,932,431, which in turn was a continuation application of Ser. No. 49,578, filed June 24, 1970, now U.S. Pat. No. 3,770,737, which application was a continuation application of Ser. No. 704,263, filed Feb. 9, 1968, now abandoned.

This invention relates to compositions of matter classified in the art of chemistry as cyclic amidines, to the processes for making and using such compositions.

The invention sought to be patented in one of its process aspects resides in the condensation reaction of an appropriate diamine with an appropriately substituted nitrile, or a functional equivalent thereof, to produce a cyclic amidine, which amidine, optionally may then be subjected to chemical oxidation.

The invention, in another of its process aspects, resides in the method of effecting an anti-depressant effect in warm-blooded animals by administering a therapeutically effective quantity of a composition of matter of this invention.

The invention, in still another of its process aspects, residents in the method of effecting an anti-inflammatory effect in warm-blooded animals by administering a therapeutically effective quantity of a composition of matter of this invention.

More particularly, this invention relates to the novel compositions of matter having the general structural formula:

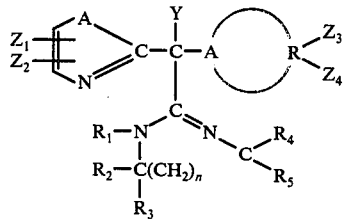

I and the pharmaceutically acceptable acid addition salts thereof, wherein $n$ is an integer of the group consisting of zero and one; A represents a member of the group consisting of $-CH=CH$, $-CH=N-$, and $-S-$; each of $Z_1$, $Z_2$ and $Z_3$ is a member of the group consisting of hydrogen, lower alkyl, trifluoromethyl, lower alkoxy and halogen and $Z_4$ is a member of the group consisting of hydrogen, lower alkyl, trifluoromethyl, lower alkoxy, halogen and diloweralkylamino,

represents a member of the group consisting of phenyl, thienyl and pyridyl, Y represents a member of the group consisting of hydrogen, lower alkyl, hydroxy, lower alkoxy and lower alkanoyloxy, $R_1$ represents a member of the group consisting of hydrogen, lower alkyl, aminoloweralkyl, hydroxyloweralkyl and aralkyl; each of $R_2$, $R_3$, $R_4$ and $R_5$ are members of the group consisting of hydrogen and lower alkyl and when taken together with the carbon atom to which they are attached, $R_2$ and $R_3$, $R_2$ and $R_4$ and $R_4$ and $R_5$ form a saturated carbocyclic ring structure having from five to seven carbon atoms.

As used herein, "lower alkyl" refers to both straight and branched chain hydrocarbon radicals having up to six carbon atoms, preferably methyl, but also including ethyl, propyl, isopropyl, n-butyl, t-butyl and the like. "Halogen" embraces all four members, although chloro and bromo are preferred "halogenoalkyl", in its more generic sense, refers to monohalogeno- and polyhalogeno- lower alkyl radicals, although those lower alkyl radicals bearing more than one of the same halogen, such as trifluoroethyl, trifluoromethyl and dichloromethyl, are preferred. "Lower alkoxy" includes those radicals having up to six carbon atoms, preferably methoxy but also including ethoxy, propoxy and the like. Aminoalkyl includes alkyl and di-alkylaminoalkyl radicals, dimethylaminopropyl and dimethylaminoethyl being preferred. The preferred dialkylamino substituent is dimethylamino, although amines having other lower alkyl radicals may similarly be employed. The preferred aralkyl 1-position radicals are benzyl and phenethyl.

"Acyl" includes such radicals as formyl, acetyl, propionyl and "acyloxy" includes those esters containing the acyl radicals of alkanoic acids containing from 2 to 6 carbon atoms. When

represents pyridyl, the 2-pyridyl and 4-pyridyl isomers are preferred. When $n$ represents zero the cyclized amidine moiety represents imidazolinyl and when $n$ represents one the cyclized amidine moiety represents 3,4,5,6-tetrahydropyrimidinyl. When A represents $-C=N$, the ring moiety represents either the pyrimidinyl or the pyrazinyl.

Pharmaceutically acceptable acid addition salts of the compounds of this invention are such salts formed with inorganic acids as hydrochloric, hydrobromic, sulfuric, phosphoric and the like acids, or with organic acids such as organic carboxylic acids, e.g. formic, acetic, propionic, glycolic, malonic, succinic, maleic, fumaric, malic, tartaric, citric, benzoic, cinnamic, salicylic, 4-aminosalicyclic, 2-phenoxybenzoic, 2-acetoxybenzoic acid and the like, or organic sulfonic acids, e.g. methane sulfonic, ethane sulfonic, 2-hydroxyethane sulfonic, ethane 1,2-disulfonic, benzene sulfonic, p-toluene sulfonic, naphthalene 2-sulfonic acid and the like. Other acid addition salts are used as intermediates, for example, in the purification of the free compounds or in the preparation of other, for example, pharmaceutically acceptable acid addition salts, as well as for identification and characterization purposes. Acid addition salts, which are primarily used for the latter are, for example those with certain inorganic acids, e.g. perchloric acid and the like, with acidic organic nitro compounds, e.g. picric, picrolonic, flavianic acid and the like, or with metal complex acids, e.g. phosphotungstic, phosphomolybdic, chloroplatinic, Reinecke acid and the like.

The compounds of this invention may be prepared from appropriately substituted nitriles by a series of analogously known methods. In a preferred method, an appropriately substituted nitrile (II), is condensed with a diamine (III) by heating the reactants together in the presence of a catalyst, such as sulfur, at temperatures of about 80°–190° C. The reaction is effected in the atmosphere of an inert gas such as nitrogen. The heating is generally continued for about 2–10 hours, although the reaction may take up to 20 hours. This step may be structurally depicted as follows:

Reaction Scheme A:

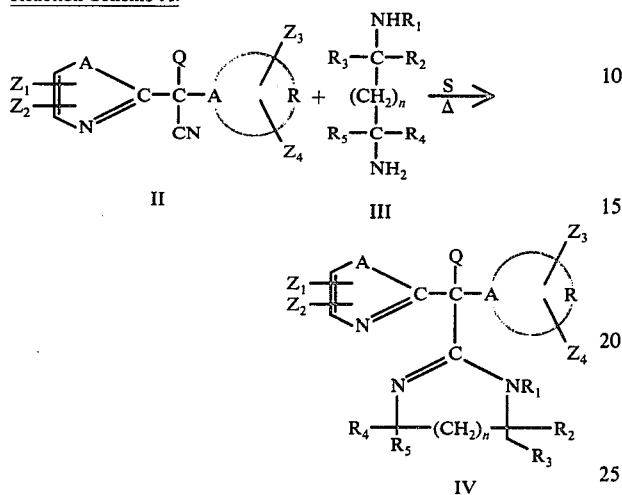

wherein $Z_1$, $Z_2$, $Z_3$, $Z_4$, A,

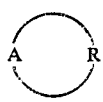

and $n$ are as previously defined in formula I and Q represents hydrogen and lower alkyl. In those instances wherein it is desired to prepare the appropriately substituted imidazoline, (i.e. when $n$ of formula IV represents 0) the diamine (III) represents a 1,2-ethylene diamine, whereas in those instances wherein it is desired to produce the appropriately substituted 3,4,5,6-tetrahydropyrimidine (i.e., when $n$ of formula IV represents 1) the diamine (III) represents a 1,3-propylene diamine. Of course, in those instances wherein it is desired to prepare either the imidazoline or the 3,4,5,6-tetrahydropyrimidine bearing the $R_1$, $R_2$, $R_3$, $R_4$ or $R_5$ substituents, said diamine reactants bear the appropriate substituent. For example, to prepare an appropriately substituted imidazoline of formula IV having an N,N-dimethylaminoethyl radical attached to the 1-position nitrogen atom of the imidazolinyl moiety, the diamine reactant used is N,N-dimethyldiethylenetriamine. Similarly, to prepare compounds of formula IV wherein $R_2$, $R_3$, $R_4$, $R_5$ each are methyl, then the diamine reactant would be 2,3-dimethyl- 2,3-butylene diamine. Likewise, in those instances wherein it is desired to produce the imidazoline compounds wherein two of said $R_2$, $R_3$, $R_4$ or $R_5$ substituents, when taken together with the carbon atoms to which they are attached, form a carbocyclic ring, e.g. when $R_2$ and $R_4$, together with the carbon atoms to which they are attached, form a cyclohexyl moiety, the diamine reactant used is 1,2-diaminocyclohexane (as a mixture of its cis and trans isomers). Alternately, the diamine (II) reactants may be used in the form of their sulfonic acid salts to yield derivatives which, upon hydrolysis, yield the desired product (IV). For example, by the employment of an ethylene diamine tosylate and by effecting the foregoing reaction there is produced the appropriately substituted imidazoline tosylate, which product, by standard techniques well known in the art, e.g., reaction with sodium hydroxide, is converted to the desired base (IV).

Alternately, the desired products (IV) may be prepared from the appropriately substituted nitriles (II) by first forming an intermediate which is then heated with the appropriate diamine to form the desired product (IV). For example, by reacting the nitrile (II) with hydrogen sulfide, or an equivalently functioning sulfide, an appropriately substituted thioamide intermediate (VI) is formed which, when then heated with a diamine of formula III there is produced the desired product (IV). In effecting this modified condensation reaction the reactants are preferably reacted in the presence of a basic catalyst such as triethylamine and N-methylpiperidine in an inert organic solvent such as dimethylformamide. This set of reactions may be structurally depicted as follows:

Reaction Scheme B:

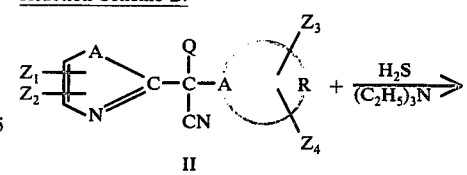

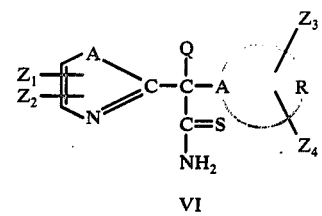

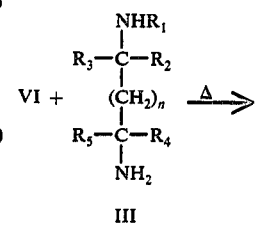

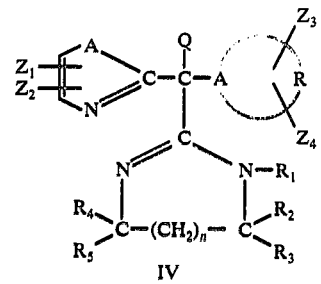

In essence, the foregoing reaction scheme represents a reactive derivative which is the functional equivalent of the cyano group (of formula II). Other such functionally equivalent reactive groups are imido-ethers, preferably in the form of their hydrohalic salts, imido-thioethers, imido halides, amidino, amido, thioamido and ester or acid halide grouping, and the like. These equivalently functioning reactive groups are represented by the formulae:

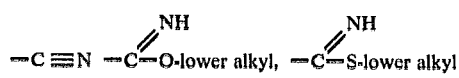

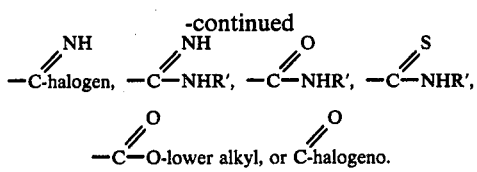

wherein halogeno preferably represents chloro, but also bromo and the like, and R' represents hydrogen or lower alkyl.

The preparation of those compounds of formula I wherein Y represents hydroxyl, is readily accomplished by standard oxidative procedures. Generally, the oxidation is effected simply by exposing a solution of the imidazolines or the 3,4,5,6-tetrahydropyrimidines of formula IV to an oxidizing atmosphere, e.g. air, at room temperature. Indeed, in those instances wherein it is desired to prepare compounds of formula I wherein Y represents hydrogen, it is advisable to prepare an acid addition salt in order to prevent auto-oxidation. Alternatively, the imidazolines and the 3,4,5,6-tetrahydropyrimidines of formula IV may be oxidized by heating these compounds in inert solvents, such as benzene, alcohol, and toluene. The oxidation of the imidazolines and the 3,4,5,6-tetrahydropyrimidines of formula IV wherein $R_1$ represents lower alkyl (or a functional equivalent thereof) is effected under conditions such as by subjecting the compounds to air while being heated (under reflux conditions) in the presence of an alkali metal alcoholate, preferably potassium t-butylate.

Esterification of the 2-hydroxyalkyl imidazolines and 2-hydroxyalkyl-3,4,5,6-tetrahydropyrimidines may readily be effected by standard procedures such as treatment of such compounds with acyl halides and anhydrides. Similarly etherification of the 2-hydroxyalkyl imidazolines and 2-hydroxyalkyl-3,4,5,6-tetrahydropyrimidines may be readily effected by standard procedures well known in the art in order to produce the desired alkoxy substituted compounds.

In general, the intermediate nitriles of formula II are known compounds, however, in those instances wherein a particular nitrile is unknown then the preparation of such intermediary nitriles is readily effected by standard and analogously known arylation procedures wherein the appropriate aryl halide, preferably aryl chloride is condensed with sodio derivatives of the appropriate nitriles. For example, the preparation of α(2-thienyl)-2-pyridylacetonitrile is effected by reacting 2-thienylacetonitrile and 2-chloropyridine in the presence of sodamide. The condensation is preferably effected in an inert solvent, e.g. toluene, liquid ammonia, benzene and the like at temperatures of from room temperature to about the reflux temperature of the reaction mixture, except when run in ammonia, then at −40° C.

The following examples illustrate the above-described methods for the preparation of compounds embraced by this invention. Such exemplifications while particularizing the details of the chemical processes of this invention are not to be construed as limiting the scope of the inventive concepts herein described.

EXAMPLE 1

α-(2-Thienyl)-2-pyridylacetonitrile

To a well-stirred solution containing 61.5 g. of 2-thienylacetonitrile and 56.5 g. of 2-chloropyridine in 400 ml. of toluene, slowly add a stirred suspension of 40 g. of sodamide in 300 ml. of toluene keeping the reaction temperature at 60°-65° C by cooling with an ice bath. After completing the addition maintain the temperature at 60° C for 2 hrs., add 200 ml. of water to the cooled reaction mixture, decant the tarry by-products and separate the aqueous layer. Evaporate in vacuo the resulting solution and dilute the thick black residue with 300 ml. of ether. Filter the separated solid and evaporate the filtrate. The desired product is distilled off at 145°-150° C/1 ml. and is recrystallized from alcohol to yield α-(2-thienyl)-2-pyridylacetonitrile, m.p. 48°-50° C.

EXAMPLE 2

α-(p-chlorphenyl)-2-thiazolylacetonitrile

At 0°-5° C add a suspension of 28.5 g. of sodamide in 300 ml. of toluene to a stirred solution containing 50 g. of p-chlorphenylacetonitrile and 40 g. of 2-chlorothiazole in 400 ml. of toluene. Maintain the temperature at 20° C for 2 hrs. and finally at 60° C for 1 hr. Consecutively add 100 ml. of water and 35 ml. of acetic acid at 0°-10° C and filter the resulting mixture. Separate the toluene layer, concentrate in vacuo and distill the residue to give α-(p-chlorphenyl)-2-thiazolylacetonitrile as a mobile yellow oil, b.p. 155°-160° C/1 mm.

EXAMPLE 3

α-Phenyl-6-chloro-2-pyridylacetonitrile

Add a suspension of 9.2 g. of sodamide in 100 ml. of toluene to 23.5 g. of benzyl cyanide and 65 g. of 2,6-dichloropyridine in 300 ml. of toluene at room temperature. Slowly heat the resulting mixture to 85°-90° C and stir the mixture at this temperature for 4.5 hrs. Cool the mixture to below 10° C and cautiously add 100 ml. of water. Separate the toluene and evaporate the toluene in vacuo. Distill the residue collecting that fraction boiling at 145°-160° / 2 ml. and crystallize the desired intermediate α-phenyl-6-chloro-2-pyridylacetonitrile from ether, m.p. 71°-73° C.

In a similar manner by substituting the appropriate reactants for those employed in the foregoing reactions and by substantially following the same procedures outlined in the above examples the following nitriles are prepared: α-(2-thienyl)-6-chloro-2-pyridylacetonitrile; α-(2-thienyl)-α-(6-chloro-2-pyridyl) propionitrile; α-(2-thienyl-α-(6-methyl-2-pyridyl) propionitrile; α-(6-methyl-2-pyridyl)-2-pyridylacetonitrile; α-phenyl-α-(2-pyrimidinyl) propionitrile; α-(p-chlorophenyl)-2-pyrazinylacetonitrile; α-(o,m-dichlorophenyl)-α-(6-methyl-2-pyridyl) propionitrile; α-(2-thienyl)-2-pyrazinylacetonitrile; α-(p-trifluoromethylphenyl)-2-pyridylacetonitrile; α-(p-methoxyphenyl)-α-(2-pyridyl) propionitrile; α-phenyl-6-methyl-2-pyridylacetonitrile; α-phenyl-3-methyl-2-pyridylacetonitrile; α-phenyl-α-(6-methyl-2-pyridyl) propionitrile; α-(p-chlorophenyl)-3-methyl-2-pyridylacetonitrile; α-phenyl-2-thiazolylacetonitrile; α-phenyl-2-pyrimidinylacetonitrile; α-phenyl-α-(2-pyrazinyl) propionitrile; α-(2-pyridyl)-α-(6-methyl-2-pyridyl) propionitrile; α-(2-pyridyl)3-methyl-2-pyridylacetonitrile; α-(2-thienyl)-2-pyrazinylacetonitrile; α-(2-thiazolyl)-α-(2-pyridyl) propionitrile; α-(p-chlorphenyl)-2-pyrimidinylacetonitrile; α-phenyl-α-(2-pyridyl) propionitrile; α-(p-methoxyphenyl)-2-pyridylacetonitrile; α-(o-chlorophenyl)-2-pyridylacetonitrile; α-(p-dimethylaminophenyl)-2-pyridylacetonitrile; α-(p-chlorophenyl)-6-chloro-2-pyridylacetonitrile; α-phenyl-6-methyl-2- pyrimidinylacetonitrile; α-phenyl-α-(6-methyl-2-pyrazinyl) propionitrile.

EXAMPLE 4

α-Phenyl-α-(2-pyridyl) thiopropionamide

With continuous stirring, subject a mixture containing 6 g. of α-phenyl-α-(2-pyridyl) propionitrile and 5 ml. of triethylamine in 60 ml. of dimethylformamide to a stream of hydrogen sulfide for 24 hours. Pour the resulting solution into 200 ml. of ice water, filter, wash and dry the solids which are formed. Recrystallize the solids from acetonitrile to obtain the intermediate α-phenyl-α-(2-pyridyl) thiopropionamide, m.p. 186°–183° C.

In a similar manner by substituting the appropriate reactants for those employed in the foregoing reaction and by substantially following the same procedure outlined in the above example, the following thioamides are prepared: α-(2-thienyl)-6-chloro-2-pyridylthioacetamide; α-(2-thienyl)-α-(6-chloro-2-pyridyl) thiopropionamide; α-(2-thienyl)-α-(6-methyl-2-pyridyl) thiopropionamide; α-(6-methyl-2-pyridyl)-2-pyridylthioacetamide; α-phenyl-α-(2-pyrimidinyl) thiopropionamide; α-(p-chlorophenyl)-2-pyrazinylthioacetamide; α-(o, m-dichlorophenyl)-α-(6-methyl-2-pyridyl) thiopropionamide; α-(2-thienyl)-2-pyrazinylthioacetamide; α-(p-trifluoromethylphenyl)-2-pyridyl-thioacetamide; α-(p-methoxyphenyl)-α-(2-pyridyl) thiopropionamide; α-phenyl-6-methyl-2-pyridylthioacetamide; α-phenyl-3-methyl-2-pyridylthioacetamide; α-phenyl-α-(6-methyl-2-pyridyl) thiopropionamide; α-(p-chlorphenyl)-3-methyl-2-pyridylthioacetamide; α-phenyl-2-thiazolylthioacetamide; α-phenyl-2-pyrimidinylthioacetamide; α-phenyl-α-(2-pyrazinyl) thiopropionamide; α-(2-pyridyl)-α-(6-methyl-2-pyridyl) thiopropionamide; α-(2-pyridyl)-3-methyl-2-pyridylthioacetamide; α-(2-thienyl)-2-pyrazinylthioacetamide; α-(2-thiazolyl)-α-(2-pyridyl) thiopropionamide; α-(p-chlorophenyl)-2-pyrimidinylthioacetamide; α-phenyl-α-(pyrazinyl) thiopropionamide; α-(p-methoxyphenyl)-2-pyridylthioacetamide; α-(o-chlorphenyl-2-pyridylthioacetamide; α-(p-dimethylaminophenyl)-2-pyridylthioacetamide; α-(p-chlorophenyl)-6-chloro2-pyridylthioacetamide; α-phenyl-6-methyl-2-pyrimidinylthioacetamide; and α-phenyl-α-(6-methyl-2-pyrazinyl) thiopropionamide.

EXAMPLE 5

2-[α-(2-Pyridyl) benzyl] imidazoline

Under a nitrogen atmosphere, carefully reflux (bath temperature of 125° C) a mixture containing 19.4 g. of 2-pyridylbenzyl cyanide, 6.6 g. of ethylene diamine and 0.2 g. of sulphur for 5 hrs. Cool the reaction mixture and under a nitrogen atmosphere dissolve the residue in 300 ml. of benzene, and water wash, dry (over anhydrous potassium carbonate) and filter the benzene solution. Concentrate the filtrate to a small volume whereupon the product crystallizes. Filter the crystals to yield 2-[α-(2-pyridyl) benzyl]-imidazoline, m.p. 134°–136° C. The maleate salt, m.p. 132°–135° C, is prepared from maleic acid and is crystallized from isopropanol.

EXAMPLE 6

2-[α-(2-Thiazolyl)-p-chlorobenzyl]-imidazoline

Under a nitrogen atmosphere, heat (110°–115° C), under reflux conditions, a mixture containing 23.5 g. of α-p-chlorphenyl-2-thiazolylacetonitrile, 7 g. of ethylene diamine and 0.2 g. of sulphur for 3 hrs. Extract the black tarry product with 200 ml. of hot benzene, cool and wash the extract with 50 ml. of water. Treat the benzene extract with a cooled solution of 4 ml. of concentrated hydrochloric acid in 25 ml. of water and separate the dark aqueous phase from the benzene. Basify the water extract with sodium carbonate and extract the precipitated oil with two 100 ml. portions of ether. Dry the ether extract and evaporate the ether to obtain 2-[α-(2-thiazolyl)-p-chlorbenzyl]-imidazoline, a viscous red product which is dissolved in acetonitrile and converted to the maleate salt which melts at 145°–147° C.

EXAMPLE 7

2-[α-(2-Pyrazinyl)-p-chlorbenzyl]-imidazoline

Under a nitrogen atmosphere, heat (130°–140° C), under reflux conditions, a mixture containing 7.5 g. of α-p-chlorphenyl-2-pyrazinyl acetonitrile (prepared from 2-chloropyrazine p-chlorphenyl acetonitrile and sodamide and refluxing toluene) 4 g. of ethylene diamine and 0.2 g. of sulphur for 8 hrs. Cool the mixture, add 100 ml. of 50:50 ether:acetonitrile, and filter the resulting mixture to remove the gummy impurities. Evaporate the filtrate to dryness, treat the residue with 600 ml. of boiling ether and concentrate the extract to 100 ml. to yield 6 g. of 2-[α-(2-pyrazinyl)-p-chlorbenzyl]-imidazoline as orange yellow plates, 113°–115° C. The maleate salt is crystallized from acetonitrile and melts at 146°–148° C.

EXAMPLE 8

1-Methyl-2-[α-(2-pyridylbenzyl]-imidazoline

Under a nitrogen atmosphere under reflux conditions, slowly heat (130° C) a mixture containing 40 g. of phenyl-2-pyridylacetonitrile, 17 g. of N-methyl ethylene diamine and 0.4 g. of sulphur for 2 hrs. and for an additional 2 hrs. at 140° C. Cool and dissolve the resulting mixture in 500 ml. of benzene. Water wash, dry (over potassium carbonate) and filter the resulting benzene solution. Concentrate the filtrate to about 75 ml. whereupon the product crystallizes on cooling. Filter the precipitate and recrystallize from ethyl acetate to yield 1-methyl-2-[α-(2-pyridylbenzyl]-imidazoline, m.p. 120°–124° C. The maleate salt is crystallized from ethyl acetate and melts at 116°–118° C.

EXAMPLE 9

2-[α-(2-Pyridyl)-α-methylbenzyl]-imidazoline

Under a nitrogen atmosphere, heat (bath at 140° C) under reflux conditions 2 g. of α-(2-pyridyl)-α-phenyl-thiopropionamide and 20 ml. of ethylene diamine. Evaporate off the excess diamine, dissolve the residue in benzene, filter, wash, dry and evaporate the benzene solution. Crystallize the residual pale green oil from isopropyl ether to yield 2-[α-(2-pyridyl)α-methylbenzyl]-imidazoline, m.p. 102–103° C. The maleate salt, crystallized from acetonitrile, melts at 156.5°–158° C.

In a similar manner by substituting the appropriate reactants for those employed in the foregoing reactions (examples 5–9) and by substantially following the same procedures outlined therein, the following imidazolines are prepared: 2-[(6-chloro-2-pyridyl) (2-thienyl)methyl]imidazoline; 2-[α(6-chloro-2-pyridyl) (2-thienyl)ethyl]imidazoline; 2[α(2-thienyl) (6-methyl-2-pyridyl)ethyl]imidazoline; 2[(5-methyl-2-pyridyl) (2-pyridyl)methyl]imidazoline; 2-[(α-(2-pyrimidinyl)-benzyl]imidazoline; 2-[α-(2-pyrazinyl)-m-chlorbenzyl]imidazoline; 2-

[α-(6-methyl-2-pyridyl)-α-methyl-o, m-dichlorbenzyl]-imidazoline; 2-[α-(2-thienyl)(2-pyrazinyl) methyl]-imidazoline; 2-[α-(2-pyridyl)-p-trifluoromethylbenzyl]-imidazoline; 2-[α-(2-pyridyl)-α-methyl-p-methoxybenzyl]imidazoline; 2-[α-(6-methyl-2-pyridyl) benzyl]-imidazoline; 2-[α-(3-methyl-2-pyridyl)benzyl]imidazoline; 2-[α-(6-methyl-2-pyridyl)-α-methylbenzyl]-imidazoline; 2-[α-(3-methyl-2-pyridyl)-p-chlorbenzyl]-imidazoline; 2-[α-(2-thiazolyl) benzyl]imidazoline; 2-[α-(2-pyrimidinyl)thienyl]imidazoline; 2-[α-(2-pyrazinyl)-benzyl]imidazoline; 2-[(2-pyridyl)(6-methyl-2-pyridyl)-methyl]imidazoline; α-[(2-pyridyl)(3-methyl-2-pyridyl) methyl]imidazoline; 2-[α(2-thiazolyl) (2-pyridyl)ethyl]-imidazoline; 2[α-(2-pyrimidinyl)-p-chlorbenzyl]-imidazoline; 2-[α-(2-pyridyl)-α-ethylbenzyl]imidazoline; 2-[α-(2-pyridyl)-p-methoxybenzyl] imidazoline; 2-[α-(2-pyridyl)-p-chlorobenzyl]imidazoline; 2-[α-(2-pyridyl)-p-dimethylaminobenzyl]imidazoline; 2-[α-(6-chloro-2-pyridyl)-p-chlorbenzyl]imidazoline; 2-[α-(6-methyl-2-pyrimidinyl)-benzyl]imidazoline; and 2-[α-(6-methyl-2-pyrazinyl-α-methylbenzyl]imidazoline.

EXAMPLE 10

1-β-Dimethylaminoethyl-2-[α-(2-pyridyl)-p-chlorbenzyl]imidazoline

Under a nitrogen atmosphere, heat (135°–140° C), under reflux conditions, a mixture containing 11.4 g. of α-p-chlorophenyl-2-pyridineacetonitrile, 6.6 g. of N,N-dimethyldiethylenetriamine and 0.2 g. of sulphur for 5 hrs. Cool the mixture, add 150 ml. of benzene, wash with 40 ml. of ice water, dry, (overy anhydrous potassium carbonate) filter, and distill off the solvent. Distill the residue in vacuo to yield 1-β-dimethylaminoethyl-2-[α-(2-pyridyl)-p-chlorobenzyl]imidazoline as a golden yellow oil, b.p. 195°–200° C/1 mm.

EXAMPLE 11

2-[(2-Pyridyl)-hydroxybenzyl]imidazoline

Dissolve 20 g. of 2-(2-pyridylbenzyl)imidazoline in 500 ml. of dry benzene and vigorously stir the solution in a current of dry air for 20 hrs. Filter the solution and concentrate the filtrate to about one-third its original volume. Filter the crystals formed on cooling of the concentrated filtrate, and recrystallize the desired product from alcohol to yield 2[(2-pyridyl)-hydroxybenzyl]-imidazoline, m.p. 152°–154° C. The hydrochloride salt, m.p. 206°–208° C, is prepared with one equivalent of dry hydrogen chloride in isopropanol.

EXAMPLE 12

2[(2-Pyridyl) (2-thienyl)-hydroxymethyl]imidazoline

Under a nitrogen atmosphere, heat (115°–120° C), under reflux conditions, a mixture containing 10 g. of 2-thienyl2-pyridylacetonitrile, 3.3 g. of ethylene diamine and 0.1 g. of sulphur for 2 hrs. Add an additional 0.5 ml. of ethylene diamine and continue heating for another 2 hours. Cool the mixture to 80° C and add 500 ml. of benzene. Water-wash, dry (over potassium carbonate) filter the resulting mixture, and subject the filtrate to a stream of dry air for 20 hours. Filter, concentrate the filtrate to dryness, and dissolve the residue in hot isopropanol. Filter while hot, cool the filtrate to give light brown crystals of 2[(2-pyridyl) (2-thienyl)hydroxymethyl]imidazoline, m.p. 151°–152° C. The maleate is crystallized from acetonitrile, m.p. 156°–157° C.

EXAMPLE 13

2[(α-6-Chloro-2-pyridyl)-α-hydroxybenzyl]imidazoline

Under a nitrogen atmosphere, heat (135°–145° C), under reflux conditions, a mixture containing 9 g. of α-phenyl-6-chloro-2-pyridylacetonitrile 2.7 g. of ethylene diamine and 0.1 g. of sulphur for 7 hrs. Cool and extract the mixture with 200 ml. of ether. Water-wash the ether extract and extract the mixture with 40 ml. of 1N hydrochloric acid. Basify the aqueous extract with excess sodium carbonate and extract the precipitated oil with 200 ml. of benzene. Dry (under anhydrous potassium carbonate) and filter the extract, and stir the dried extract in dry air for 24 hours. Filter and concentrate the filtrate to obtain a residue which is crystallized from acetonitrile to yield 2[α(6-chloro-2-pyridyl)-α-hydroxybenzyl]imidazoline, m.p. 154°–156° C.

EXAMPLE 14

2[α(2-Pyridyl-α-hydroxybenzyl]-4,5,6,7,8,9-hexahydrobenzimidazole

Under a nitrogen atmosphere, heat (180°–190° C), under reflux conditions, a mixture containing 21 g. of α-phenyl-2-pyridineacetonitrile, 25 g. of 1,2-diamino cyclohexane (a mixture of cis and trans isomers) and 0.2 g. of sulphur for 7 hrs. Cool and dissolve the mixture in 500 ml. of ether, filter the ether and extract the filtrate with 50 ml. portions of 1N hydrochloric acid. Basify the aqueous extract with excess sodium carbonate and extract the precipitated oil with 200 ml. of ether to obtain the crystalline product 2[α(2-pyridyl)-α-hydroxybenzyl]-4,5,6,7,8,9-hexahydrobenzylimidazole which is dissolved in 100 ml. of benzene and the resulting solution is stirred in dry air for 20 hrs., filtered and concentrated to dryness. The so obtained 2[α(2-pyridyl)-α-hydroxybenzyl]-4,5,6,7,8,9-hexahydrobenzimidazole, when converted to the maleate salt from acetonitrile, melts at 152°–154° C.

EXAMPLE 15

1-Acetyl-2[(2-pyridyl)-hydroxybenzyl]imidazoline

Dissolve 12.8 g. of 2[(2-pyridyl)hydroxybenzyl] imidazoline in 25 ml. of dioxane and, with vigorous stirring, slowly add 2.4 ml. of acetic anhydride in a drop-wise fashion. After each 0.5 ml. addition warm the solution to 60° C for 5 min. and then cool the solution to 20° C before adding additional anhydride. Continue the stirring for 20 hours, filter the precipitated acetate salt and concentrate the resulting filtrate to about 10 mls. Recrystallize the desired product from alcohol to yield 1-acetyl-2[(2-pyridyl)-hydroxybenzyl]imidazoline, m.p. 150°–153° C.

EXAMPLE 16

1-Methyl-2[α(-2-pyridyl)hydroxybenzyl]imidazoline

Add 5 g. of 1-methyl-2-(2-pyridylbenzyl)imidazoline and 25 ml. of dimethyl sulfoxide to a solution of potassium t-butylate (prepared from 1.4 g. of potassium and 200 ml. of t-butanol) and stir the resulting solution in a stream of dry air for 30 hrs. Add 2.1 ml. of acetic acid to the resulting mixture and remove the alcohol in vacuo. Shake the residue with 200 ml. of benzene and 50 ml. of cooled 5 sodium carbonate. Separate the benzene phase, water-wash, dry, filter and evaporate in vacuo. Recrystallize the residue from isopropanol acetate to yield 1-methyl-2[α(-2-pyridyl) hydroxybenzyl]imidazoline, m.p. 105°–108° C.

Similarly, by substantially following the oxidation procedures outlined above with the appropriate reactants, there are also produced: 2-[α-(2-thiazolyl)-p-chlorhydroxybenzyl]-imidazoline; 2-[α(2-pyrimidinyl)-m-chlorhydroxybenzyl]-imidazoline; 1-ethyl-2-[α-(2-pyridyl)hydroxybenzyl]-imidazoline; 2-[(6-chloro-2-pyridyl) (2-thienyl)hydroxymethyl]imidazoline; 2-[(6-methyl-2-pyridyl) (2-pyridyl)hydroxymethyl]imidazoline; 2-[(α-(2-pyrazinyl)-α-hydroxybenzyl]imidazoline; 2-[α(2-pyrazinyl)-p-chlorhydroxybenzyl]imidazoline; 2-[α-(6-methyl-2-pyridyl)-o,m-dichlorhydroxybenzyl]-imidazoline; 2-[α-(2-thienyl)-α-(2-pyrazinyl)hydroxymethyl]imidazoline; 2-[α-(2-pyridyl-p-trifluoromethyl-hydroxybenzyl]imidazoline; 2-[α-(2-pyridyl)-p-methoxyhydroxybenzyl]imidazoline; 2-[α-(6-methyl-2-pyridyl) hydroxybenzyl]imidazoline; 2-[α-(3-methyl-2-pyridyl)-hydroxy-benzyl]imidazoline; 2-[α-(3-methyl-2-pyridyl)-p-chlorhydroxy-benzyl]imidazoline; 2-[α-(2-thiazolyl)-hydroxybenzyl]imidazoline; 2-[α(2-pyrimidinyl)hydroxythienyl]imidazoline; 2-[α-(2-pyrazinyl) hydroxybenzyl]imidazoline; 2-[(2-pyridyl)(6-methyl-2-pyridyl) hydroxymethyl]imidazoline; 2-[(2-pyridyl)(3-methyl-2-pyridyl) hydroxymethyl]imidazoline; 2-[α-(2-pyrimidinyl)-p-chlorhydroxy-benzyl]imidazoline; 2-[α-(2-pyridyl)-p-methoxyhydroxybenzyl] imidazoline; 2-[α-(2-pyridyl-p-chlorhydroxybenzyl]imidazoline; 2-[α-(2-pyridyl)-p-dimethylaminohydroxybenzyl]imidazoline; 2-[α-(6-methyl-2-pyrimidinyl)-hydroxybenzyl]-imidazoline; 1-β-dimethyl-aminoethyl-2-[α-(2-pyridyl)-p-chlorhydroxybenzyl]imidazoline; 2-[α-(2-thiazolyl)-p-chlorhydroxybenzyl],3,4,5,6-tetrahydro-pyrimidine; 2-[α-(2-pyrimidinyl)-p-chlorhydroxybenzyl]-3,4,5,6-tetrahydropyrimidine; 1-methyl-2-[α-(2-pyridyl)hydroxybenzyl]-3,4,5,6-tetrahydropyrimidine; 2-[(6-chloro-2-pyridyl) (2-thienyl) hydroxymethyl]-3,4,5,6-tetrahydropyrimidine; 2-[(6-methyl-2-pyridyl) (2-pyridyl)hydroxymethyl]-3,4,5,6-tetrahydropyrimidine; 2-[(α-(2-pyrimidinyl)-α-hydroxybenzyl]3,4,5,6-tetrahydropyrimidine; 2-[α-(2-pyrazinyl)-p-chlorhydroxybenzyl]3,4,5,6-tetrahydropyrimidine; 2-[α(6-methyl-2-pyridyl)-o,m-dichlorohydroxybenzyl]-3,4,5,6-tetrahydropyrimidine; 2-[α(2-thienyl)-α-(2-pyrazinyl)hydroxymethyl]-3,4,5,6-tetrahydropyrimidine; 2-[α-(2-pyridyl)-p-trifluoromethylhydroxybenzyl]3,4,5,6-tetrahydropyrimidine; 2-[α-(2-pyridyl)-p-methoxyhydroxybenzyl]-3,4,5,6-tetrahydropyrimidine; 2-[α-(6-methyl-2-pyridyl)hydroxybenzyl]-3,4,5,6-tetrahydropyrimidine; 2-[α-(3-methyl-2-pyridyl)hydroxybenzyl]3,4,5,6-tetrahydropyrimidine; 2-[α-(3-methyl-2-pyridyl)-p-chlorhydroxybenzyl]-3,4,5,6-tetrahydropyrimidine; 2-[α-(2-thiazolyl)hydroxybenzyl]-3,4,5,6-tetrahydropyrimidine; 2-[α-(2-pyrimidinyl) hydroxybenzyl]-3,4,5,6-tetrahydropyrimidine; 2-[α-(2-pyrazinyl) hydroxybenzyl]-3,4,5,6-tetrahydropyrimidine; 2-[(2-pyridyl) (6-methyl-2-pyridyl)hydroxymethyl]-3,4,5,6-tetrahydropyrimidine; α-[(2-pyridyl) (3-methyl-2-pyridyl)hydroxymethyl]-3,4,5,6-tetrahydropyrimidine; 2-[α(2-pyrimidinyl)-p-chlorhydroxybenzyl]-3,4,5,6-tetrahydropyrimidine; 2-[α(2-pyridyl)-p-methoxyhydroxy-benzyl]-3,4,5,6-tetrahydropyrimidine; 2-[α(2-pyridyl)-p-chlorhydroxybenzyl]-3,4,5,6-tetrahydropyrimidine; 2-[α(2-pyridyl)-p-dimethylaminohydroxybenzyl]-3,4,5,6-tetrahydropyrimidine; 2-[α-(6-methyl-2-pyrimidinyl)hydroxybenzyl]-3,4,5,6-tetrahydropyrimidine; 1-β-dimethylaminoethyl-2-[α-(2-pyridyl)-p-chlorhydroxybenzyl]-3,4,5,6-tetrahydropyrimidine; 2[(2-pyridyl) (2-thienyl)-hydroxymethyl]-3,4,5,6-tetrahydropyrimidine; 2[(α-6-chloro-2-pyridyl)-α-hydroxybenzyl]-3,4,5,6-tetrahydropyrimidine 1-acetyl-2[(2-pyridyl)-hydroxybenzyl]-3,4,5,6-tetrahydropyrimidine and 1-methyl-2[(α-2-pyridyl)hydroxybenzyl]-3,4,5,6-tetrahydropyrimidine.

As stated above, the method of achieving an anti-depressant effect in warm-blooded animals is effected by administering a therapeutically effective quantity of a compound of this invention (as defined by formula I). The therapeutically effective quantity of a compound of this invention (I) may readily be ascertained by standard and well-known techniques in the art. One such laboratory technique for the determination of anti-depressant activity is a Tetrabenazine Antagonism assay similar to that described by V. G. Vernier, et al., p.683, in "Psychosomatic Medicine" edited by J. H. Nodine and J. H. Moyer, 1962, as follows: Group of 10 male Carworth Farm (CF No. 1) mice are orally administered the test compound and 30 minutes after administration of the test drug the mice are intraperitoneally injected with 30 milligrams per kilogram of body weight of tetrabenazine methane sulfonate. After thirty minutes the test compound is evaluated for the degree of ptosis developed in the mice. A rating scale of 0-4 is employed with 4 representing a normal palpebral opening, and scores of 3,2,1 and 0 represent slight, moderate, marked and complete closure of the palpebral opening (ptosis), respectively. Based upon ratings with compounds known to exhibit significant anti-depressant effects, as well as compounds known not to exhibit anti-depressant effects, a rating of 2 or more is considered to be indicative of a significant anti-depressant activity. From the foregoing test procedures and by other standard laboratory techniques, as well as by comparison with well-known anti-depressant agents, the therapeutically effective anti-depressant dosage range for the compounds of this invention for achieving an anti-depressant effect is 0.5–30 mg/kg. of body weight. Although it is expected that a therapeutically effective dosage will be orally administered in 3–4 divided doses, the actual total daily dosage will depend upon the degree of severity of the depression of the warm-blooded animal, its cause and other health factors. Thus, in each specific instance the attending diagnostician will determine the actual dosage frequency and degree of anti-depression sought to be achieved.

As is true for most classes of therapeutically effective compounds, certain sub-classes are found to be more effective than others. The preferred sub-classes of compounds of this invention which are particularly useful are those of which the following compounds are specific members thereof: 2-[phenyl-2-(pyridyl)-hydroxymethyl]imidazoline-hydrochloride; 2-[(2-pyridyl)-2-thienyl)-hydroxymethyl]imidazoline maleate; 2-[α(2-pyridyl)-p-chlorobenzyl]imidazoline maleate; 2-[p-chlorophenyl-2-(pyridyl)-hydroxymethyl]imidazoline maleate; 2[(α-hydroxy)-α-(2-pyridyl)-m-chlorobenzyl]-imidazoline maleate; 2-(2-pyridylbenzyl)imidazoline maleate; 2[(α-hydroxy)-α-(2-pyridyl)-p-methoxybenzyl]imidazoline maleate; 2[(bis-2-pyridyl)-hydroxymethyl]imidazoline maleate; 2[(α-hydroxy)-α-(2-pyrimidinyl)-4-chlorobenzyl]imidazoline maleate; 2-[(6-chloro-2-pyridyl)-phenylhydroxymethyl]imidazoline maleate, with the first five being the most preferred.

It is another aspect of this invention that the tangible embodiments of this invention, as defined by formula I, also exert an anti-inflammatory effect in warm-blooded animals by administering a therapeutically effective quantity of a compound of this invention. The therapeutically effective quantity of a compound of this invention for achieving an anti-inflammatory effect is readily ascertained by the standard and well-known Carrageenin Induced Inflammation (Carrageenin Paw) Test, as well as by comparison with other known non-steroidal anti-inflammatory agents. Another specific method employed is the acute Carrageenin Paw assay which is a modification of Winter, C. A., Risley, E. A. and Nuss, G. W., 1963, "Anti-inflammatory and anti-pyretic activities of indomethacin, 1-(p-chlorobenzoyl)-6-methoxy-2-methylindole-3-acetic acid," J. Pharm. and Exptl. Therap. 141:369–376, described as follows: Female rats (Charles River CD strain), weighing 140–150 grams, were treated orally with the test compound. One hour later, 0.05 ml. of a 1% solution of carrageenin, the phlogistic agent, was injected into the plantar surface of the right hind paw and the volume of the paw determined. Three hours later, the paw volume was determined again. The difference in paw volume between the two times is defined as the degree inflammation. Paw volumes, expressed in grams, are measured by immersing the foot in a mercury bath tared on a balance to an ink mark which has been placed at the level of the lateral malleolus. The immersion of the paw to the specified point causes the balance to record a change in weight which is directly proportional to the mercury displaced (Archimedes principle). Thus, the weight in grams of the displaced mercury is directly related to the paw volume. From these tests it is determined that the therapeutically effective quantity for achieving an anti-inflammatory test is 30–100 mg/kg of body weight.

In addition to the above-mentioned functional use characteristics, the compounds of this invention may also be used in the treatment of Parkinson's Disease. In this applied use the compounds may be administered in the form of pharmaceutical formulations such as are illustrated above or else they may be utilized in combination with 3-(3,4-dihydroxyphenyl)-L-alanine and lower alkanoyl esters of 3-(3,4-dihydroxyphenyl)-L-alanine. In accordance with the standard assay procedures such as are described in Science, 166, 889–901, 1969, the compounds have been found to be effective in the treatment of Parkinson's Disease by the administration of about 0.1 to 3 mg/kg on a daily basis. In those instances wherein the compounds of this invention are co-administered with 3-(3,4-dihydroxyphenyl)-L-alanine or the lower alkanoyl esters of 3-(3,4-dihydroxyphenyl)-L-alanine, it is to be found that the normal maintenance dosage level of 3-(3,4-dihydroxyphenyl)-L-alanine and/or the lower alkanoyl esters of 3-(3,4-dihydroxyphenyl)-L-alanine will be substantially lowered when used as agents for the treatment of Parkinson's Disease.

In their function as therapeutically useful compounds, it is advantageous to administer the compounds to the host animal in admixture with an acceptable pharmaceutical carrier suitable for enteral or parenteral administration, said carrier constituting a major portion of the admixture. Such preparations may be in such forms, as for example, tablets, capsules and suppositories, or in liquid forms as for example, elixirs, emulsions and injectables. In the formulation of pharmaceutical preparations there can be employed such substances which do not react with the active substance as for example, water, gelatin, lactose, starches, magnesium stearate, calcium carbonate, talc, vegetable oils, benzyl alcohols, gums, polyalkylene glycols, petroleum jelly and the like. The active ingredient of such pharmaceutical preparations is preferably present in the preparation in such proportions by weight that the proportion by weight in the active ingredient to be administered lies between 0.1% and 50%.

TABLET FORMULATION

The following formulation provides for the manufacture of 1,000 tablets:

|     |                                                                           | Grams |
| --- | ------------------------------------------------------------------------- | ----- |
| (1) | 2-[p-Chlorophenyl-2-(pyridyl)-hydroxymethyl]imidazoline maleate           | 25    |
| (2) | Lactose, U.S.P.                                                           | 181   |
| (3) | Corn Starch, U.S.P.                                                       | 92.5  |
| (4) | Magnesium Stearate                                                        | 1.5   |

Thoroughly granulate a mixture of 92.5 g. of corn starch and the lactose with a paste prepared by dissolving 20 gm. of corn starch in 100 ml. of hot distilled water. Dry the resulting granulation at 40°–45° C and pass it through a No. 16 mesh screen. To the dried, screened granulation add a blended mixture of the active ingredient (1) and the magnesium stearate. Thoroughly blend and then press into tablets of 300 mg. each.

CAPSULE FORMULATION

The following formulation provides for the manufacture of 1,000 capsules:

|     |                                                                           | Grams |
| --- | ------------------------------------------------------------------------- | ----- |
| (1) | 2-[n-Chlorophenyl-2-(pyridyl)-hydroxymethyl]imidazoline maleate           | 25    |
| (2) | Lactose                                                                   | 273.5 |
| (3) | Magnesium stearate                                                        | 1.5   |

Mix active ingredient (1) with the lactose and blend in the magnesium stearate. Fill hard gelatin capsules with 300 mg. each of the blended mixture to produce capsules containing 25 mg. of 2-[p-chlorophenyl-2-(pyridyl)-hydroxymethyl]imidazoline maleate.

PARENTERAL FORMULATION

The following formulation provides for the manufacture of 1,000 vials each containing 10 mg. of active ingredient:

|     |                                                                              | Grams |
| --- | ---------------------------------------------------------------------------- | ----- |
| (1) | 2-[p-chlorophenyl-2-(pyridyl)-hydroxymethyl]imidazoline maleate gm          | 10.0  |
| (2) | Monobasic potassium phosphate gm                                             | 6.0   |
| (3) | Water for injection, U.S.P. q.s. liter                                       | 1.0   |

Dissolve ingredients (1), (2), and (3) in approximately 80 percent of the volume of water and filter the resulting solution. Add to the filtrate sufficient water to make to a 1000 ml. volume. Sterile-filter the solution and asceptically fill one milliliter portions of the so-prepared solution into two milliliter vials, then lyophylize. After the lyophilized cake is dry, asceptically stopper the vials with rubber plugs and seal.

I claim:

1. The process for eliciting an anti-depressant effect which comprises administering to a mammal suffering from mental depression a therapeutically effective quantity of a compound selected from the group consisting of a cyclic amidine of the structural formula:

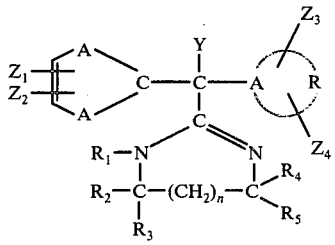

and a pharmaceutically acceptable acid addition salt thereof, wherein $n$ is an integer of the group consisting of zero and one; A is a member of the group consisting of —C=C,—C=N and —S— wherein A together with the ring atoms to which it is attached represents a heterocycle of the group consisting of pyridyl, pyrimidinyl, pyrazinyl and thiazoyl each of $Z_1$, $Z_2$, and $Z_3$ is a member of the group consisting of hydrogen, lower alkyl, trifluoromethyl, lower alkoxy and halogen and $Z_4$ is a member of the group consisting of hydrogen, lower alkyl, trifluoromethyl, lower alkoxy, halogen and diloweralkylamino;

represents a member of the group consisting of phenyl, thienyl and pyridyl; Y represents a member of the group consisting of hydrogen, lower alkyl, hydroxy, lower alkoxy and lower alkanoyloxy containing 2 to 6 carbon atoms; $R_1$ represents a member of the group consisting of hydrogen, lower alkyl, aminolower alkyl, hydroxyloweralkyl, benzyl and phenethyl; each of $R_2$, $R_3$, $R_4$ and $R_5$ are members of the group consisting of hydrogen and lower alkyl.

2. A process of claim 1 wherein Y is hydroxy.
3. A process of claim 1 wherein $n$ is zero.
4. A process of claim 1 wherein Y is phenyl.
5. A process of claim 2 wherein A is pyridyl.
6. A process of claim 3 wherein A is pyridyl.
7. A process of claim 4 wherein A is pyridyl.
8. A process of claim 5 wherein $n$ is zero.
9. A process of claim 8 wherein

is phenyl.

10. A process of claim 8 wherein

is pyridyl.

11. A process of claim 8 wherein

is thienyl.

12. A process of claim 9 wherein all of $R_2$, $R_3$, $R_4$, $R_5$, $Z_1$, $Z_2$, $Z_3$ and $Z_4$ are hydrogen.
13. A process of claim 12 wherein $R_1$ is hydrogen.
14. A process of claim 12 wherein $R_1$ is lower alkyl.
15. A process of claim 14 wherein $R_1$ is methyl.
16. A process of claim 1 wherein Y is hydroxy, A is pyridyl, each of $Z_1$, $Z_2$, $Z_3$, $Z_4$, $R_1$, $R_2$, $R_3$, $R_4$ and $R_5$ is hydrogen,

is phenyl and $n$ is zero, said compound being 2-[(2-pyridyl)-hydroxybenzyl]imidazoline.

* * * * *

UNITED STATES PATENT OFFICE
CERTIFICATE OF CORRECTION

Patent No. 4,081,544                    Dated March 28, 1978

Inventor(s) Lewis A. Walter

It is certified that error appears in the above-identified patent and that said Letters Patent are hereby corrected as shown below:

Column 7, line 13, "186°-183°" should read ---186°-188°---.
Column 14, line 33, "(1) 2/n-chlorophenyl-" should read
---(1) 2/p-chlorophenyl- ---.
Column 15 (In the Diagram)

should read $$Z_1 \atop Z_2 = \!\!\!\!\Bigl\langle\begin{matrix} A \\ \diagdown \\ N \end{matrix} C -$$

Signed and Sealed this

Seventeenth Day of October 1978

[SEAL]

Attest:

RUTH C. MASON
Attesting Officer

DONALD W. BANNER
Commissioner of Patents and Trademarks